US011372017B2

(12) United States Patent
German et al.

(10) Patent No.: US 11,372,017 B2
(45) Date of Patent: Jun. 28, 2022

(54) MONOCULAR VISUAL-INERTIAL ALIGNMENT FOR SCALED DISTANCE ESTIMATION ON MOBILE DEVICES

(71) Applicant: Charles River Analytics, Inc., Cambridge, MA (US)

(72) Inventors: Stan German, Cherry Hill, NJ (US); Michael Kim, Cambridge, MA (US); Henry Roth, Boston, MA (US)

(73) Assignee: Charles River Analytics, Inc., Cambridge, MA (US)

( * ) Notice: Subject to any disclaimer, the term of this patent is extended or adjusted under 35 U.S.C. 154(b) by 3 days.

(21) Appl. No.: 17/001,120

(22) Filed: Aug. 24, 2020

(65) Prior Publication Data

US 2021/0140990 A1     May 13, 2021

Related U.S. Application Data

(60) Provisional application No. 62/890,349, filed on Aug. 22, 2019.

(51) Int. Cl.
| | |
|---|---|
| *G01P 7/00* | (2006.01) |
| *G06T 7/50* | (2017.01) |
| *G06T 7/246* | (2017.01) |
| *G01P 15/08* | (2006.01) |
| *G06T 5/00* | (2006.01) |
| *H04W 88/02* | (2009.01) |

(52) U.S. Cl.
CPC ............... *G01P 7/00* (2013.01); *G01P 15/08* (2013.01); *G06T 5/006* (2013.01); *G06T 7/246* (2017.01); *G06T 7/50* (2017.01); *G06T 2207/30241* (2013.01); *H04W 88/02* (2013.01)

(58) Field of Classification Search
USPC ................................. 382/103, 294, 106–107
See application file for complete search history.

(56) References Cited

U.S. PATENT DOCUMENTS

| | | |
|---|---|---|
| 2010/0321490 A1 | 12/2010 | Chen et al. |
| 2015/0317070 A1 | 11/2015 | Lammers Van Toorenburg et al. |
| 2016/0061582 A1 * | 3/2016 | Lucey .................. G01B 11/022 348/137 |
| 2016/0131751 A1 | 5/2016 | Mathews et al. |
| 2017/0061195 A1 | 3/2017 | Li et al. |

(Continued)

OTHER PUBLICATIONS

Mustaniemi et al., Inertial-Based Scale Estimation for Structure from Motion, arXiv: 1611.09498v2 [cs.CV], Aug. 11, 2017, pp. 1-8.*

(Continued)

*Primary Examiner* — Ishrat I Sherali
(74) *Attorney, Agent, or Firm* — Daly, Crowley, Mofford & Durkee, LLP

(57) ABSTRACT

Methods, techniques, apparatus, and algorithms are described for robustly measuring real-world distances using any mobile device equipped with an accelerometer and monocular camera. A general software implementation processes 2D video, precisely tracking points of interest across frames to estimate the unsealed trajectory of the device, which is used to correct the device's inertially derived trajectory. The visual and inertial trajectories are then aligned in scale space to estimate the physical distance travelled by the device and the true distance between the visually tracked points.

16 Claims, 6 Drawing Sheets

(56) References Cited

U.S. PATENT DOCUMENTS

2018/0232947 A1     8/2018    Nehmadi et al.
2020/0033128 A1     1/2020    Baratz et al.

OTHER PUBLICATIONS

Solin et al. PIVO: Probabilistic Inertial-Visual Odometry for Occulsion-Robust Navigation, arXiv: 1708.00894v2 [cs.CV] Jan. 23, 2018, pp. 1-10. (Year: 2018).*

Tang et al., Toward autonomous navigation using an RGB-D camera for flight in unkown indoor enviornment, 2014 IEEE 978-1-4799-0/14, pp. 2007-2012. (Year: 2014).*

Muratov et al., 3D: Capture: 3D Reconstruction for a smartphone, 2016 IEEE 978-1-5090-1437-8/16, pp. 893-900. (Year: 2016).*

International Search Report and Written Opinion dated Nov. 19, 2020 for International Application No. PCT/US2020/047626 filed Aug. 24, 2020 for Charles River Analytics, Inc., 16 pages.

Choi, J., Medioni, G., Lin, Y., Silva, L., Regina, O., Pamplona, M., and Faltemier, T. C. (2010). 3D face reconstruction using a single or multiple views. In Pattern Recognition (ICPR), 2010 20th International Conference on, 3959-3962.

Ding, C. and Tao, D. (2015). A comprehensive survey on pose-invariant face recognition. arXiv preprint arXiv:1502.04383.

Galantucci, L. M., Percoco, G., and Di Gioia, E. (2009). Low cost 3D face scanning based on landmarks and photogrammetry. In Intelligent Automation and Computer Engineering, 93-106.

Hassner, T., Harel, S., Paz, E., and Enbar, R. (2015). Effective face frontalization in unconstrained images. In Proceedings of the IEEE Conference on Computer Vision and Pattern Recognition, 4295-4304.

Jo, J., Choi, H., Kim, I.-J., and Kim, J. (2015). Single-view-based 3D facial reconstruction method robust against pose variations. Pattern Recognition, 48, 73-85.

Kemelmacher-Shlizerman, I. and Basri, R. (2011). 3d face reconstruction from a single image using a single reference face shape. Pattern Analysis and Machine Intelligence, IEEE Transactions on, 33, 394-405.

Liu, F., Zeng, D., Li, J., and Zhao, Q. (2015). Cascaded regressor based 3d face reconstruction from a single arbitrary view image. arXiv preprint arXiv:1509.06161.

Zollhöfer, M., Martinek, M., Greiner, G., Stamminger, M., and Süßmuth, J. (2011). Automatic reconstruction of personalized avatars from 3D face scans. Computer Animation and Virtual Worlds, 22, 195-202.

Notification of International Preliminary Report, International Preliminary Report and Written Opinion, dated Mar. 3, 2022,International Application No. PCT/US2020/047626, 10 pages.

* cited by examiner

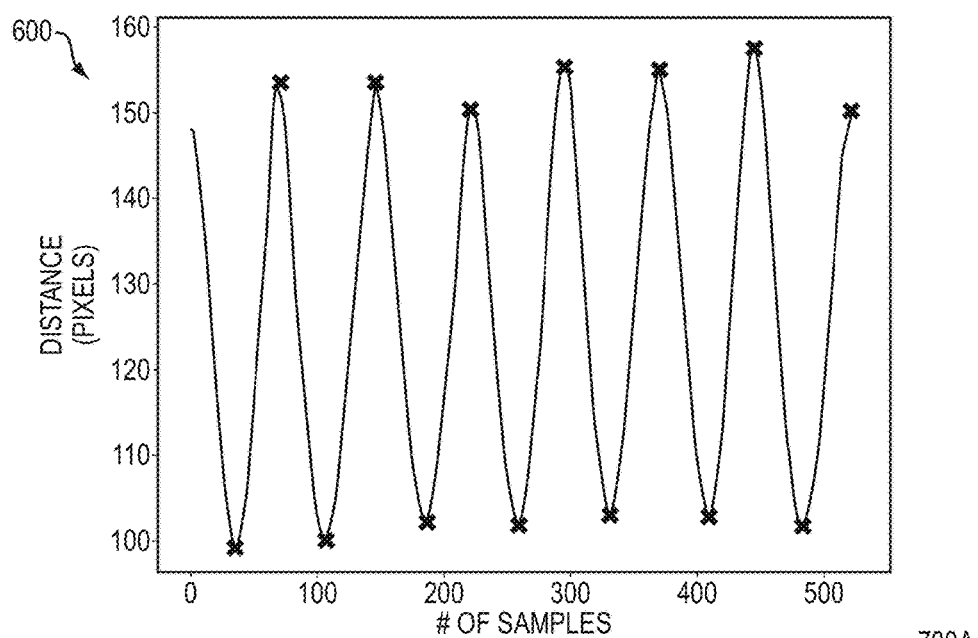
FIG. 6
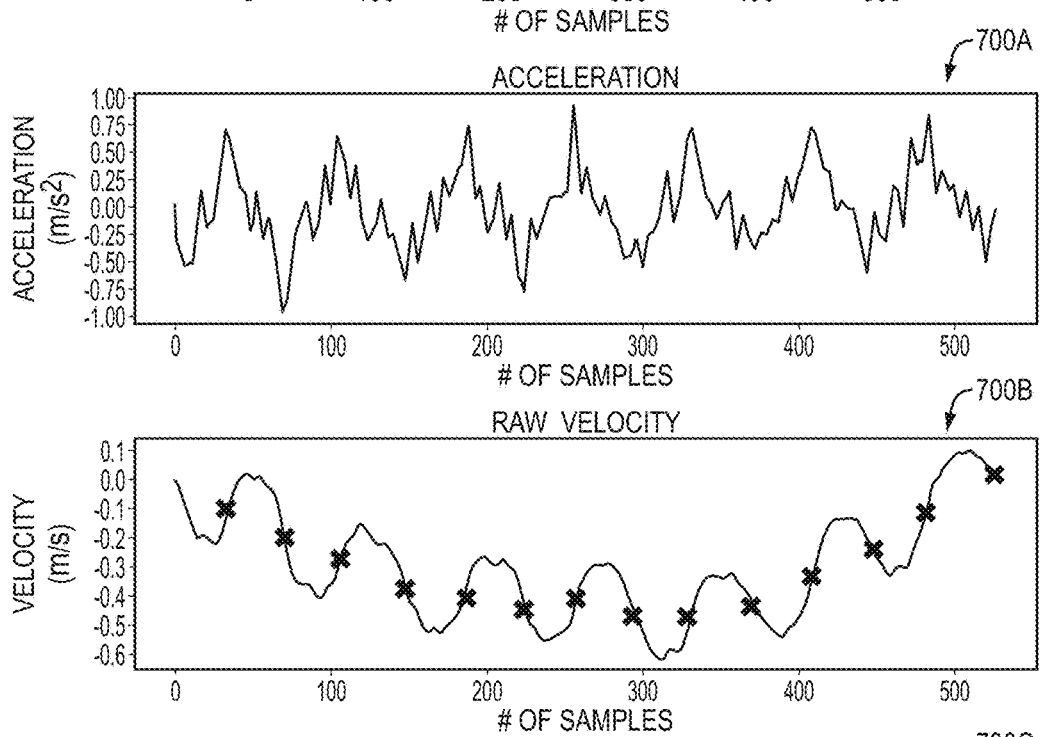
FIG. 7A
FIG. 7B
FIG. 7C

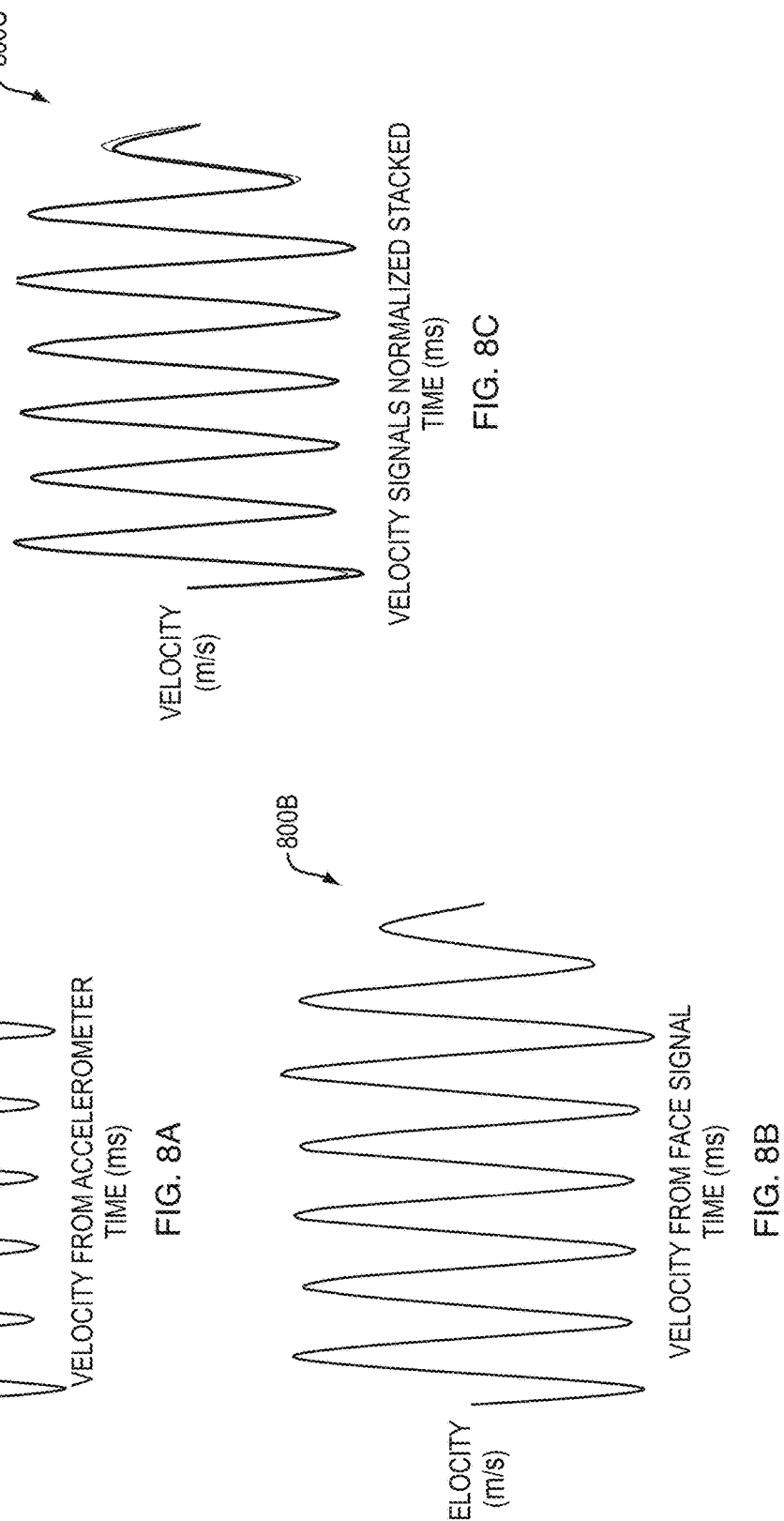
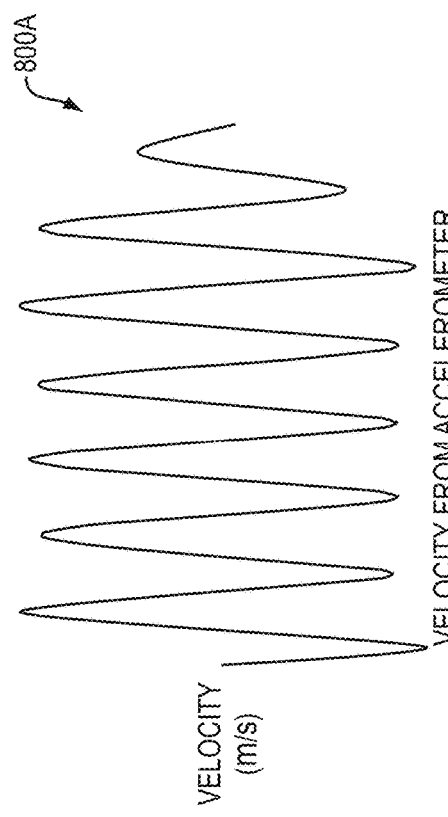
FIG. 8A — VELOCITY FROM ACCELEROMETER TIME (ms)
FIG. 8B — VELOCITY FROM FACE SIGNAL TIME (ms)
FIG. 8C — VELOCITY SIGNALS NORMALIZED STACKED TIME (ms)

MONOCULAR VISUAL-INERTIAL ALIGNMENT FOR SCALED DISTANCE ESTIMATION ON MOBILE DEVICES

CROSS-REFERENCE TO RELATED APPLICATION

This application is based upon and claims priority to U.S. provisional patent application 62/890,349, entitled "Monocular Visual-Inertial Alignment for Scaled Distance Estimation on Mobile Devices," filed 22 Aug. 2019. The entire content of the noted provisional application is incorporated herein by reference.

STATEMENT REGARDING FEDERALLY SPONSORED RESEARCH

This invention was made with government support under contract numbers W911SR-16-C-0030, W911SR-17-C-0058, and W911SR-19-C-0046 awarded by the U.S. Army. The government has certain rights in the invention.

BACKGROUND

Technical Field

This disclosure relates generally to measuring distances using camera techniques and more particularly to measuring distances using monocular techniques.

Description of Related Art

A key challenge in the development of an easy-to-use, low-cost tool for assessing respirator fit is the ability to automatically perform real-world anthropometric measurements. Developments in the computer vision community over the last decade have paved a promising way forward, enabling fine-grained 3D reconstruction of the human face and head. Most reconstruction techniques use 3D sensors, such as the Microsoft Kinect, to localize facial landmarks (e.g., tip of nose, inner corner of right eye) in depth images (Ding and Tao, 2015; Jo, Choi, Kim et al., 2015; Zollhofer, Martinek, Greiner et al., 2011), but require specialized hardware and suffer from sensor limitations, such as poor outdoor performance. More promising are those approaches that do not require specialized sensors and rely solely on ubiquitous 2D cameras, such as those found in smartphones. Photogrammetric techniques, such as Structure From Motion, use multiple views of the human face to infer 3D structure through correspondence, but are sensitive to slight facial deformations across views and require large-scale camera motion. As a result, these methods typically require several cameras to simultaneously capture multi-view information (Choi, Medioni, Lin et al., 2010; Galantucci, Percoco, and Di Gioia, 2009). Alternatively, single image data-driven techniques (Kemelmacher-Shlizerman and Basri, 2011; Hassner, Harel, Paz et al., 2015; Liu, Zeng, Li et al., 2015) eliminate the multi-camera requirement, but are susceptible to viewpoint ambiguities (e.g., nose protrusion is ambiguous from a frontal view without ideal lighting conditions) and cannot directly infer object scale.

Estimating an object's physical dimensions from a monocular image requires additional information beyond that obtainable from imagery alone. One common approach to estimating real-world scale from a monocular camera is to use a Structure From Motion (SFM) technique, which integrates motion signals from an inertial measurement unit (IMU) with motion parallax cues extracted across multiple images. While these approaches have been leveraged successfully for many applications, including in the field of robotics, they are often inadequate for mobile applications (e.g., self-scanning facial anthropometries, such as pupillary distance, using a smartphone camera).

SFM typically performs poorly when device motion is restricted: large-scale motion creates a wider array of trackable image features (or landmarks) and increases accelerometer excitation, which increases the signal-to-noise ratio (SNR). SFM typically requires higher quality (i.e., more expensive) inertial measurement units (IMUs). IMUs, especially those ubiquitous in mobile devices, typically have poorer noise characteristics compared to more expensive IMUs that SFM approaches are designed for. SFM also requires robust tracking of many repeatable image features: certain objects, such as the human face, have limited textures that are difficult to track using traditional SFM feature tracking techniques, leading to inadequate quantities of trackable features. Scale estimates derived from SFM are also sensitive to slight deformations in object appearance across views due to this reliance on large feature sets.

SUMMARY

The present disclosure provides algorithms methods, systems, apparatus, and components for robustly measuring real-world distances using any mobile device equipped with an accelerometer and monocular camera. In accordance with an aspect of the present disclosure, a general software implementation processes 2D video, precisely tracking points of interest across frames to estimate the unsealed trajectory of the device, which is used to correct the device's inertially derived trajectory. The visual and inertial trajectories are then aligned in scale space to estimate the physical distance travelled by the device and the true distance between the visually tracked points.

Exemplary embodiments of the present disclosure are directed to algorithms, methods, systems, apparatus, and components which are tailored for handheld mobile devices and enable real-world distance measurement by aligning visual velocities derived from an image-based feature detector with inertial trajectories extracted from an accelerometer. Implemented embodiments have been successfully used for the sizing and fitting of respirator masks also the measurement of pupillary distance using a smartphone camera, meeting optometry standards for accuracy without requiring a reference object, such as a credit card.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 6 shows an example of a 1-D visual trajectory signal marked with an x in locations where the velocity of the device is zero.

FIGS. 7A-7C depict: in (A) filtered z-axis acceleration; (B) velocity derived from acceleration; x-marker: locations of zero velocity based on the visual trajectory signal, according to an embodiment of the present disclosure; and (C) corrected velocity based on visual signal.

FIGS. 8A-8C are three plots depicting a pair of velocity signals, one (A) derived from the visual signal and the other (B) from an IMU signal, that are highly correlated with each other as shown in their overlay plot (C).

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

One aspect of the present disclosure includes an estimation framework that incorporates an image processing pipeline that estimates a 1-D visual trajectory from sequences of paired landmarks (e.g., image pupil positions) extracted from video of an object. The 1-D visual trajectory is determined-through post-processing or via real-time processing, as computational resources permit- and fused with an inertial trajectory captured by the device's IMU to produce accurate scale estimates for real-world measurements (e.g., facial anthropometries, pupillary distance). Unlike standard SFM approaches, which require a large pool of repeatable features, the approach of the present disclosure only relies on a single pair of repeatable features (e.g., image position of pupil centers) and is computationally efficient enough to be run on a smartphone. The reduction and simplification compared to standard SFM approaches is possible by regression fitting the present disclosure's novel scale estimation results to relative distances of image features. It has been shown that the resulting equation can be used to estimate real-world feature distances with less than 3% error when applied to facial anthropometries. Embodiments of the present disclosure can also utilize a novel filtering approach to mitigate the effects of sensor drift, which are typical with IMU-based approaches.

Figure 1:
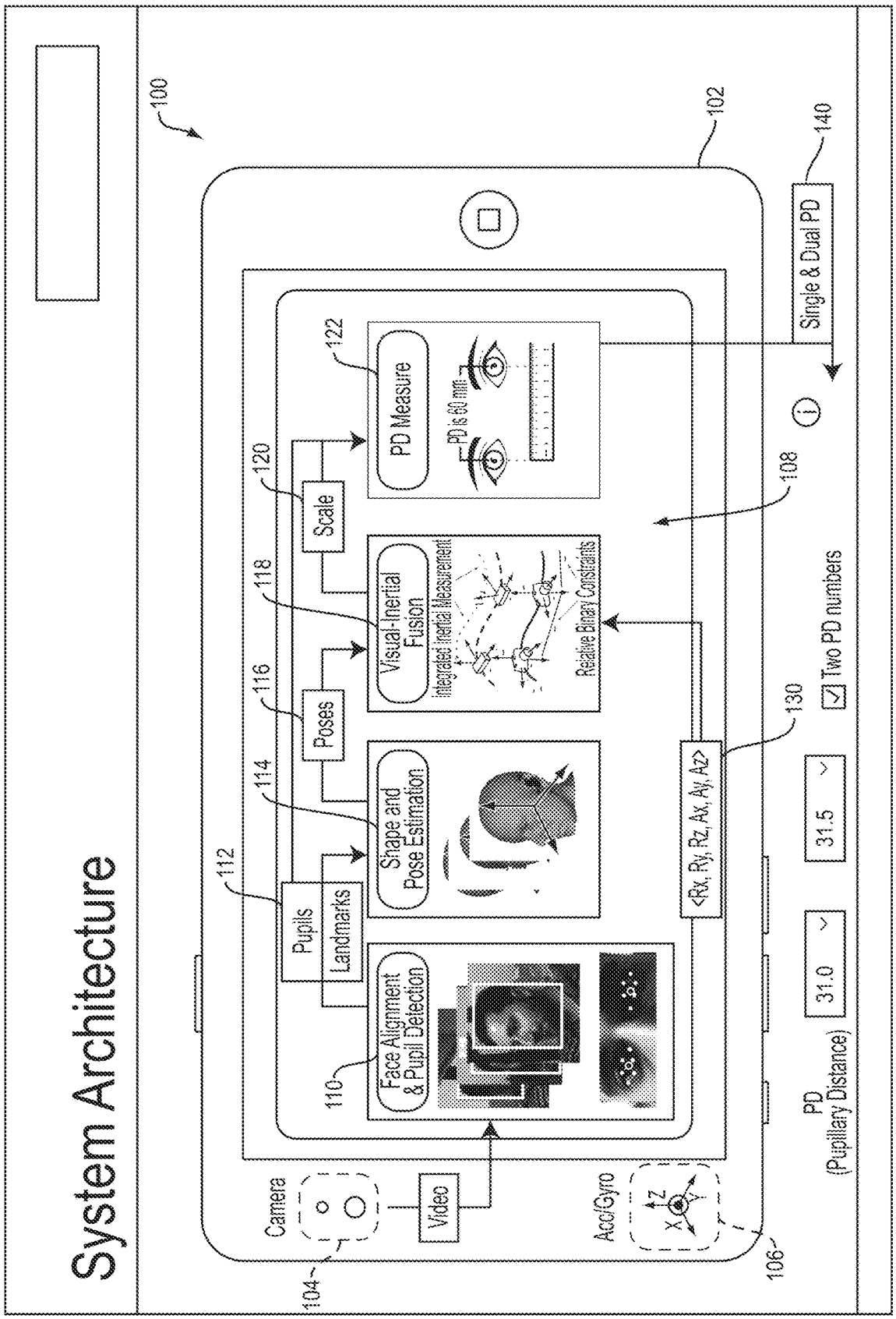
FIG. 1 depicts a system architecture according to an exemplary embodiment of the present disclosure.

FIG. 1 depicts architecture of a system 100 according to an exemplary embodiment of the present disclosure. System 100 includes a smartphone 102 having a camera 104, an IMU 106 (denoted by "Acc/Gyro"), and a touchscreen 108. Examples of suitable smartphones include but are not limited to: Apple iPhone 8, iPhone 8 Plus, iPhone X, iPhone XR, and iPhone 11; Motorola Razr, moto, moto G6, moto G6 Play, moto G7; and Samsung Galaxy S20, Galaxy S20 Ultra, Galaxy Z Flip. Galaxy A70, Galaxy A71. Other smart devices may of course be used within the scope of the present disclosure.

Figure 2:
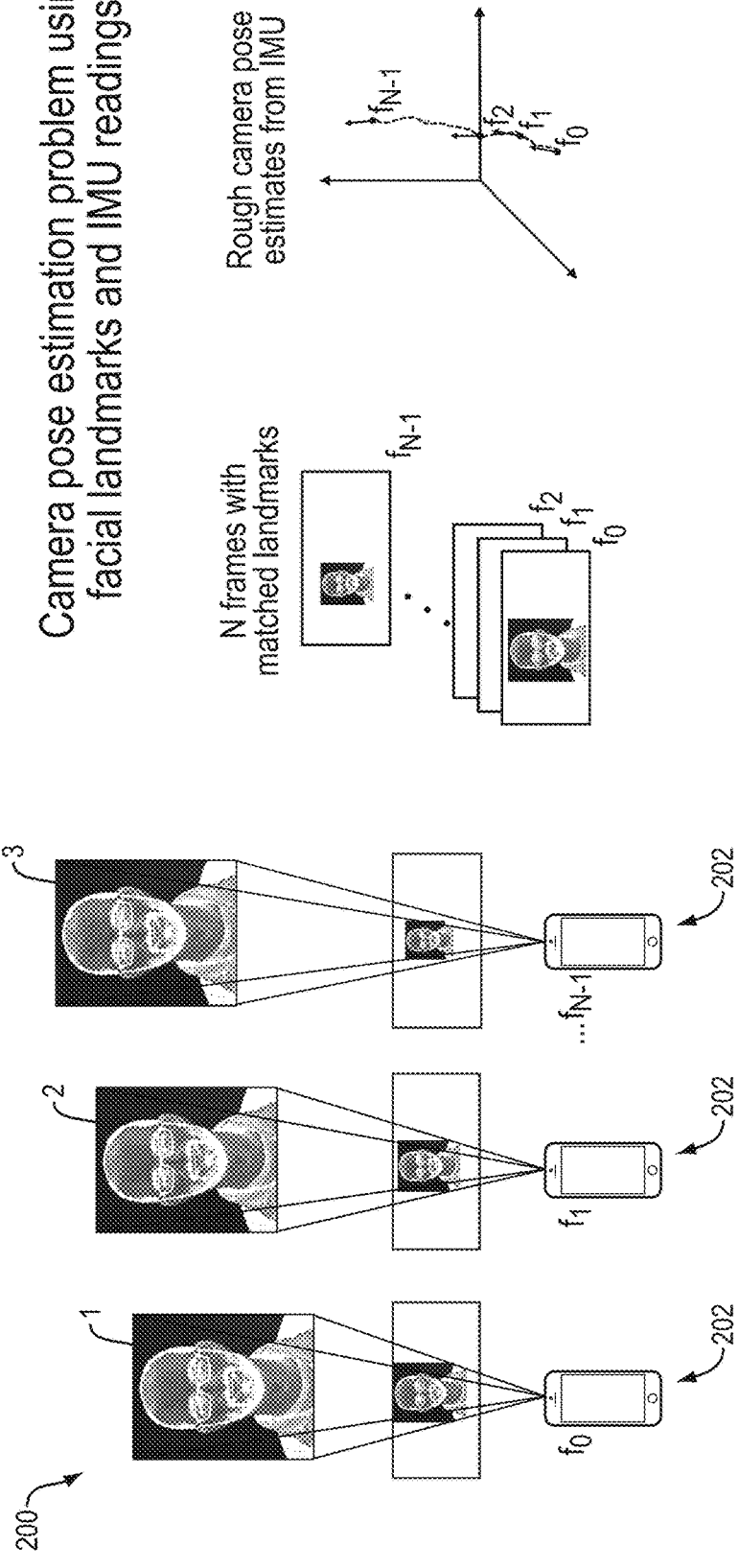
FIG. 2 depicts an exemplary visual-inertial fusion process in accordance with the present disclosure.

FIG. 2 depicts an exemplary visual-inertial fusion process 200 in accordance with the present disclosure. In the plot showing rough camera pose estimates from an IMU (at far right), all axes are in units of meters.

Figure 3:
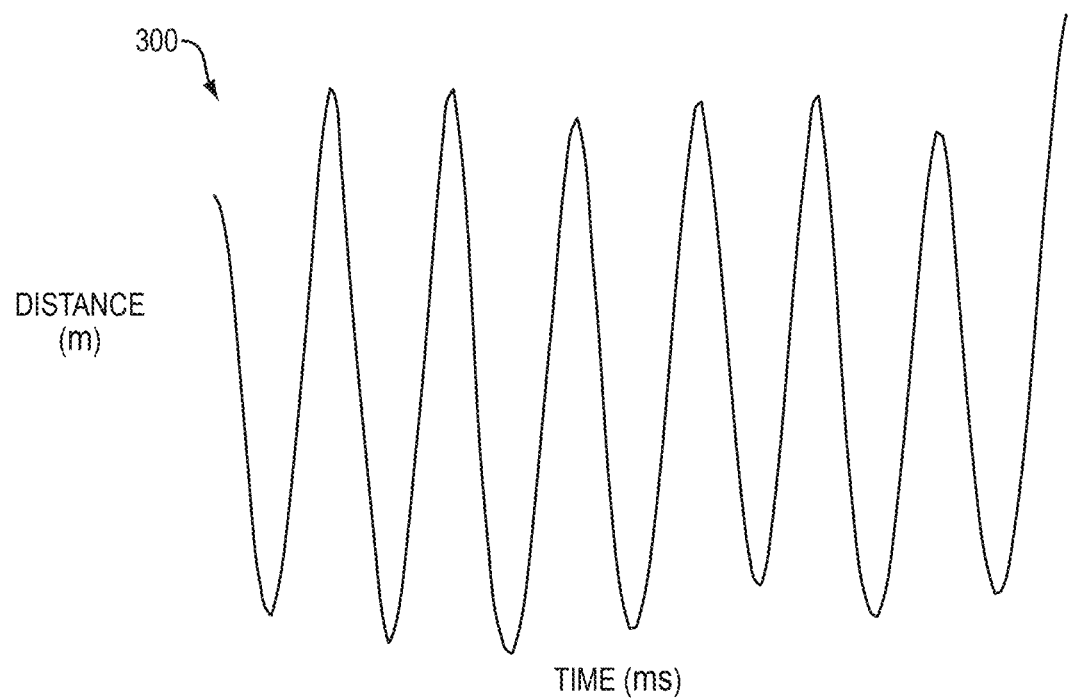
FIG. 3 depicts ideal motion plotted as a function of z-motion distance from an object of interest.

One key aspect of the present disclosure is the use of a cyclical motion pattern that enables the fusion of IMU and derived image data. The motion of the data capture is focused on the z-axis (the device moving toward and away from the object). The ideal motion plotted as a function of z motion distance from an object of interest is shown (as 300) in FIG. 3. In the figure, the vertical axis represents distance (in meters) while the horizontal axis represent time (in milliseconds). The motion does not need to be strictly sinusoidal but preferably does fit certain constraints, e.g., with motion$_z$>>motion$_x$ and motion$_z$>>motion$_y$. For linear motion, the z-axis motion should be dominant (i.e., x-axis and y-axis power are less than z-axis power). As long as this constraint is met, any non-z-axis motion is marginalized.

The rotation of the camera relative to the object being observed (e.g., a face) preferably will stay within limit$_{rotation}$ and is also affected by the camera placement and field of view. Each rotational component, $\varphi$ (roll) $\theta$ (pitch) $\Psi$ (yaw), preferably is below certain values for the best accuracy, e.g., with limit$_\varphi$<$\varphi$<limit$_\varphi$ and limit$_\theta$<$\theta$<limit$_\theta$ and limit$_\Psi$<$\Psi$<limit$_\Psi$.

As the described approach segments each cycle of z-axis motion, these constraints on motion only need to be met within the entirety of a single cycle. Any motion segment that passes both constraints can be used in the data fusion step.

A 1-D signal is generated from the sequence of object images by detecting a pair of repeatable features, for example, a user's 2D pupil positions. The pixel position of each feature is first undistorted using a radial distortion model:

$$x_u = (x_d - x_c)(k_1 r^2 + k_2 * r^4 \ldots) \quad \text{(EQ. 1)}$$

$$y_u = (y_d - y_c)(k_1 r^2 + k_2 * r^4 \ldots) \quad \text{(EQ. 2)}$$

where,
$x_d, y_d$=the distorted locations of the feature
$x_u, y_u$=the feature locations after distortion is removed
$x_c, y_c$=the distortion centers
$k_1, k_2, \ldots k_n$=the distortion coefficients $$r = \sqrt{(x_d - x_c)^2 + (y_d - y_c)^2} \quad \text{(EQ. 3)}$$

For the above equations, it may be noted that radial distortion can be modeled as an infinite series. For applications such as described herein, use of two distortion parameters (i.e., terms in the series expansion) can be sufficient.

Figure 4:
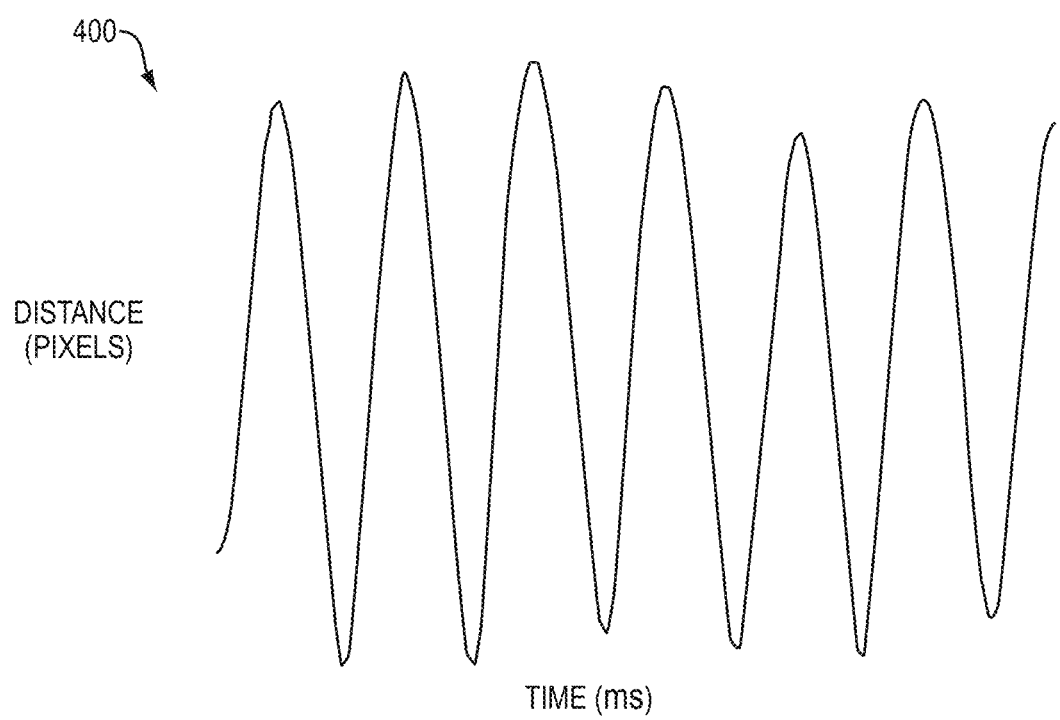
FIG. 4 shows an example of a 1-D visual trajectory signal produced by pupil feature pairs.

To generate the 1-D signal, the distance between the undistorted pixel coordinates of the feature pairs are calculated:

$$\text{signal}_{visual}(n) = \sqrt{(f1_x(n) - f2_x(n))^2 + (f1_y(n) - f2_y(n))^2} \quad \text{(EQ. 4)}$$

where,
n=the number of frames in the sequence
$f1_x, f1_y$=the x and y location of feature 1
$f2_x, f2_y$=the x and y location of feature 2
signal$_{visual}$=the 1-D visual trajectory FIG. 4 shows an example of a 1-D visual trajectory signal 400 produced by pupil feature pairs. In the figure, the vertical axis represents distance (in pixels) while the horizontal axis represent time (in milliseconds). The signal is inversely correlated with the distance away from the object.

All sensor data, including the visual trajectory, is put through a low-pass filtering (e.g., wavelet) and down-sampling process before signal analysis and visual-inertial fusion. Prior to signal filtering, each signal is resampled to a matched sampling rate. The original visual signal has a sampling rate based on the framerate of the camera, typically somewhere in the range of 24 Hz and 60 Hz on a typical mobile phone. The IMU's accelerometer and gyroscope, typically have larger sampling rates, somewhere in the range of 60-200 HZ depending on the model of the phone. Preferably all sensor data is resampled to a consistent sampling rate (e.g., 60 Hz) prior to filtering.

Figure 5A:
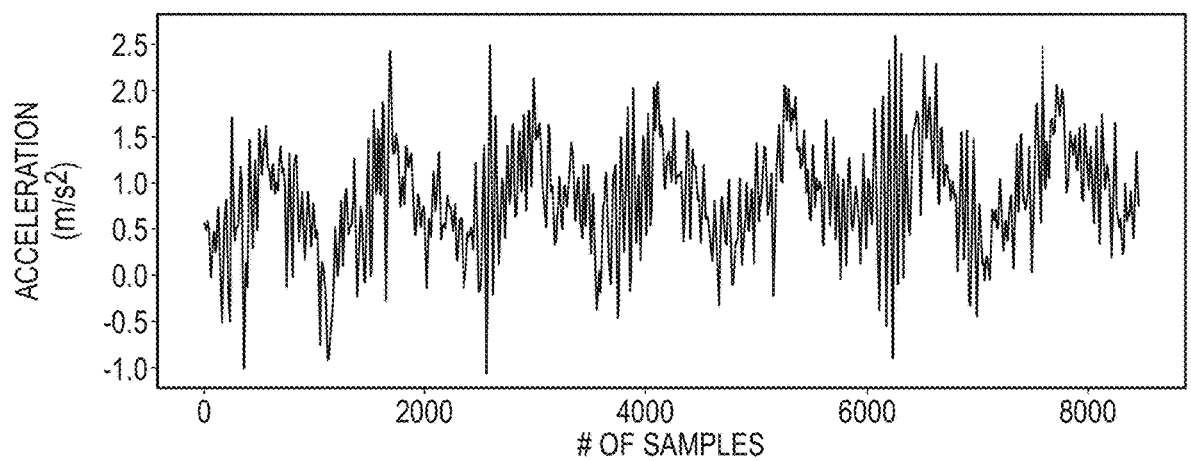
FIGS. 5A-5B depict sensor filtering in accordance with an exemplary embodiment of the present disclosure.
Figure 5B:
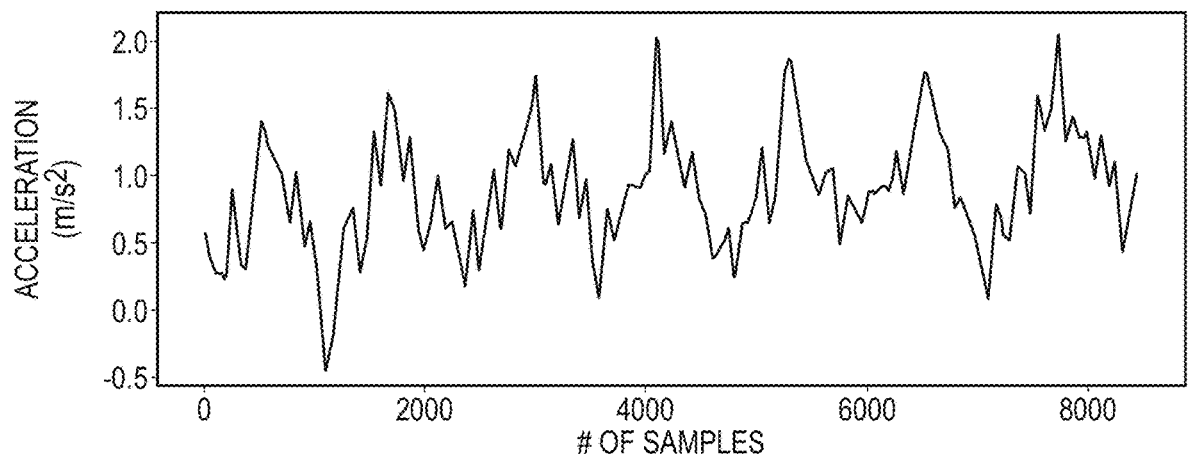

Initial noise filtering is performed by wavelet threshold filtering. First, all signals are decomposed into a multi-band representation. Each band is then filtered based on thresholding coefficients that have been calculated from test data for each phone. Once filtered, the signal is recreated based on the filtered bands. Although the key frequencies during data collection are quite low, the signals are kept at a consistent sampling rate for offset and bias processing. Example results 500A-500B are shown in FIGS. 5A-B. In the figures, the vertical axes represent acceleration (meters per second squared) while the horizontal axes represent number of samples.

The next step is calculating the time offset between the inertial and visual trajectory signals. First the accelerometer data from the z-axis is converted to velocity values through integration and the visual signal is converted to velocity values through derivation. The velocity values are filtered, e.g., using IIR filters, to remove both the signal bias and noise. Using the filtered signals, a normalized cross correlation is performed to compare both signals:

$$NCC(m) = \frac{\sum_{n=0}^{N-m-1} x(n) \cdot x(n+m)}{\sqrt{\sum_{n=0}^{N-m-1} x^2(n) \cdot \sum_{n=0}^{N-m-1} x^2(n+m)}} \quad \text{(EQ. 5)}$$

The sample (m) with the highest NCC match dictates the calculated offset between the video and IMU.

As with any IMU signal, regardless of the quality, producing accurate velocity and position estimates is difficult as both are based on the integration of acceleration. Any noise, Gaussian noise or bias, leads to sensor drift, causing the errors to grow larger over time. A novel approach of the present disclosure solves the problem of drift by extracting accurate estimates of where in time z velocity is zero based on the visual trajectory signal. The visual trajectory signal is generated based on a feature pair that has a pixel distance that is inversely correlated with the motion away from the object, producing a very clean signal that can be used to determine where the device changes direction (i.e., has zero velocity). FIG. 6 shows an example of the face signal marked with an x in locations where the velocity of the device is zero.

FIG. 6 is a plot 600 of a visual trajectory signal and locations of zero (o) motion velocity (x marker) based on data collection. In the figure, the vertical axis represents distance (pixels) while the horizontal axis represents number of samples.

Once the times are obtained where the velocity should be zero, the velocity estimates can be altered based on the acceleration to account for the drift. FIGS. 7A-7C depict in (A) a plot 700A of a filtered z-axis acceleration (in meters per second squared); (B) a plot 700B f a velocity (m/s) derived from acceleration; and, (C) a plot 700C of a constrained velocity (m/s) based on visual signal; x-marker: locations of zero (o) velocity based on the visual trajectory signal. The horizontal axes represent number of samples.

FIG. 7B shows a velocity based on the acceleration signal from FIG. 7A The x markers indicate the times in the visual trajectory signal where the velocity is zero, which also means that the velocity based on motion should also be zero. Once the corrections are made, an accurate estimate of motion with sensor drift removed is produced as shown on the bottom plot (700C). For future reference, the interval between two estimated zero velocities can be considered a single cycle.

For accurate scale estimation, the data collection procedure preferably passes certain criteria: rotation limits, feature detection outliers, cycle speed, and cycle length. Rather than discarding the entire collection, the approach partitions each cycle (i.e., the interval between the 0 velocities) based on the criteria. The post-processed/drift-compensated velocity signal, gyro estimates, along with the visual trajectory signal are used for cycle pass analysis. While only the passing cycles are used for final analysis, the signals are kept whole for additional signal processing.

For scale estimation, z velocities are estimated for both the visual and inertial trajectory signals. The visual trajectory signal is converted to a velocity signal using the following equation:

$$A(t) = f(\text{signal}_{visual}(t), \text{camera}_{intrinsics}) \quad \text{(EQ. 6)}$$

$$L(t) = \frac{1}{\left(2 * \tan\frac{A(t)}{2}\right)}$$

$$\text{velocity}_{visual}(t) = \frac{dL}{dt}$$

The signal produced by the equation is now an unscaled (and unfiltered) version of the accelerometer-based velocity. For an exemplary embodiment, based on experimentation, only a small range of frequencies are needed for accurate scale estimation during handheld capture. The ranges between 0.3 Hz and 2 Hz were observed to provide the best performance due to the trade-offs between accelerometer excitation, which perform better at faster speeds, and image blurring, which is stronger with faster motion. These ranges have been extensively tested with a large user population and is the ideal range for data collection. The pair of velocity signals, one derived from the visual signal and the other from the IMU signal, are put through a suitable filter, e.g., an IIR filter tuned to these ranges, producing two signals that are highly correlated with each other. A Butterworth filter is one (non-limiting) example of a suitable IIR filter. An example is shown in FIG. 8.

FIGS. 8A-8C are three plots 800A-800C depicting a pair of velocity signals, one (in FIG. 8A) derived from the visual signal and the other (in FIG. 8B) from an IMU signal, that are highly correlated with each other as shown in their overlay plot (in FIG. 8C). The vertical axes in FIGS. 8A-8C represent velocity (m/s) while the horizontal axes represent time (ms).

The final scale estimate is calculated as follows:

$$s = \{x \in \mathbb{R} : a < x < b\} \quad \text{(EQ. 7)}$$

$$\text{scale} = \min_s \frac{1}{N} \sum_{i=0}^{N-1} (vel_{visual} - vel_{inertial})^2$$

$a = $ minimum acceptable scale range $b = $ minimum acceptable scale range

Using this calculated scale value, a (e.g., lab calibrated) regression fit equation can be used to estimate the final true distance. For an implemented embodiment, the technique described produced results with less than 3% error.

While embodiments of the present disclosure have been described and implemented for facial anthropometries, other embodiments can be applied to other 3D body measurements and can also be generalized to measure distances between any two (2) fixed points in the real-world.

Exemplary embodiments of the present disclosure are robust to low data rates and shallow motions, is extremely lightweight, can run in a mobile web browser, is precise, and is able to measure distance between any two tracked points.

Exemplary embodiments of the present disclosure can use, provide, or rely upon the following in any combination: image correction; feature detection variations (facial landmark detection, pupil detection, feature point detectors, manually initialized points of interest); feature tracking; 3D Pose Estimation variations (e.g., known 3D to 2D correspondence); and/or, visual-inertial alignment (correction of inertial signal based on unsealed visual correspondence).

Exemplary embodiments of the present disclosure can include the following features in any combination: Feature detection, e.g., implemented as facial landmark detection or as pupil detection under pupillary distance (PD) measurement tool; object or physical feature tracking; 3D Pose Estimation; and/or, visual-inertial alignment.

Unless otherwise indicated, the embodiments for distance measurement that have been discussed herein are implemented with a specially-configured computer system specifically configured to perform the functions that have been described herein for the component. Each computer system includes one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

Each computer system for distance measurement may include, consist of, or be part of a desktop computer or a portable computer, such as a laptop computer, a notebook computer, a tablet computer, a PDA, a smartphone, or part of a larger system, such a vehicle, appliance, and/or telephone system. Each computer system may include one or more computers at the same or different locations. When at different locations, the computers may be configured to communicate with one another through a wired and/or wireless network communication system.

Each computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

For example, the embodiments of the present disclosure can be implemented on any electronic device or collection of devices that integrate an accelerometer and a monocular camera (including use of a single camera where multiple are present). The embodiments of the present disclosure describe a system for measuring the distance between two points but can be applied to many pairs of points simultaneously to mitigate noise and improve accuracy. Additional embodiments could include the deep integration of a gyroscopic signal to correct for non-linear motion of the device and reduce device rotation constraints during data collection.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

What is claimed is:

1. A method, using a mobile device equipped with a camera and an inertial measurement unit (IMU), for measuring real-world distance between two or more points in an image, the method comprising:
   aligning estimated visual and inertial trajectories;
   converting the visual and inertial trajectory signals into velocity signals; and
   scale aligning the velocity signals by minimizing their Euclidean distance.

2. The method of claim 1, wherein a plug-in image-based feature tracker is used to estimate visual trajectories.

3. The method of claim 2, wherein the feature tracker is specific to known object landmarks or a generic feature tracker.

4. The method of claim 1, wherein the mobile device follows a cyclical motion pattern during data capture.

5. The method of claim 4, wherein the motion has additional constraints on device rotation and velocity that are actively monitored and corrected by software.

6. The method of claim 1, wherein image distortion is corrected prior to feature tracking.

7. The method of claim 1, wherein the visual and inertial trajectory signals are preprocessed through standard filtering and time alignment.

8. The method of claim 1, wherein the inertial trajectory signal drift is corrected via zero velocity detection in the visual trajectory signal.

9. A processor system for measuring real-world distance using a mobile device equipped with a camera and an inertial measurement unit (IMU), the system comprising:
   a processor; and
   a memory unit in communication with the processor via a communication infrastructure and configured to store processor-readable instructions;
   wherein, when executed by the processor, the processor-readable instructions cause the processor to:
   align estimated visual and inertial trajectories;
   convert the visual and inertial trajectory signals into velocity signals; and
   scale align the velocity signals by minimizing their Euclidean distance.

10. The system of claim 9, wherein a plug-in image-based feature tracker is used to estimate visual trajectories.

11. The system of claim 10, wherein the feature tracker is specific to known object landmarks or a generic feature tracker.

12. The system of claim 9, wherein the mobile device follows a cyclical motion pattern during data capture.

13. The system of claim 12, wherein the motion has additional constraints on device rotation and velocity that are actively monitored and corrected by software.

14. The system of claim 9, wherein image distortion is corrected prior to feature tracking.

15. The system of claim 9, wherein the visual and inertial trajectory signals are preprocessed through standard filtering and time alignment.

16. The system of claim 9, wherein the inertial trajectory signal drift is corrected via zero velocity detection in the visual trajectory signal.

* * * * *